United States Patent [19]

Hansenne

[11] Patent Number: 5,679,656
[45] Date of Patent: Oct. 21, 1997

[54] ARTIFICIAL TANNING COMPOSITIONS COMPRISING DIHYDROXYACETONE/ ALKYLPOLYSACCHARIDES/FATTY ALCOHOLS

[75] Inventor: Isabelle Hansenne, Paris, France

[73] Assignee: L'Oreal, Paris, France

[21] Appl. No.: 567,280

[22] Filed: Dec. 5, 1995

[30] Foreign Application Priority Data

Dec. 5, 1994 [FR] France .................. 94 14593

[51] Int. Cl.$^6$ .................. A61K 31/70; A61K 31/715
[52] U.S. Cl. .................. 514/54; 514/25; 514/53; 514/57; 514/59; 514/60; 514/844
[58] Field of Search .................. 514/25, 53, 54, 514/57, 59, 60, 844

[56] References Cited

U.S. PATENT DOCUMENTS 5,171,577  12/1992  Griat et al. .................. 424/450

FOREIGN PATENT DOCUMENTS 0382619  8/1990  European Pat. Off. .
9316683  9/1993  WIPO .

Primary Examiner—John Kight
Assistant Examiner—Everett White
Attorney, Agent, or Firm—Burns, Doane, Swecker & Mathis, L.L.P.

[57] ABSTRACT

Improvedly stable and effective, topically applicable cosmetic compositions well suited for artificially tanning and/or darkening human skin, comprise, in a cosmetically acceptable vehicle, diluent or carrier therefor, an effective artificial tanning amount of dihydroxyacetone, in immixture with at least one alkylpolysaccharide and at least one fatty alcohol, and, optionally, at least one polysaccharide.

24 Claims, No Drawings

ARTIFICIAL TANNING COMPOSITIONS COMPRISING DIHYDROXYACETONE/ ALKYLPOLYSACCHARIDES/FATTY ALCOHOLS

BACKGROUND OF THE INVENTION

1. Technical Field of the Invention

The present invention relates to novel cosmetic compositions for topical application, for the artificial tanning and/or darkening of the skin (such compositions sometimes being referred to as self-tanning compositions), and also to the use of same for the cosmetic application indicated above.

The present invention more especially relates to artificial suntan compositions having improved activity and stability and which comprise, in a cosmetically acceptable vehicle, diluent or carrier, dihydroxyacetone as the self-tanning agent, in immixture with one or more alkylpolysaccharides, in particular alkylpolyglucosides, and one or more fatty alcohols.

2. Description of the Prior Art

It is known to this art that dihydroxyacetone, or DHA, is a particularly advantageous compound which is currently employed in cosmetics as an agent for the artificial tanning of the skin. When applied to the skin, especially to the face, it elicits a tanning or darkening effect, the appearance of which is similar to that which may result from prolonged exposure to the sun (natural tan) or under a UV lamp. When used as such, moreover, it presents the advantage of totally avoiding the risks of skin or cutaneous reaction which are generally associated with the aforesaid prolonged exposures (erythema, burns, loss of suppleness, appearance of wrinkles, premature aging of the skin, and the like).

However, one of the disadvantages of the known self-tanning compositions based on DHA is that the intensity of the coloration obtained on the skin and/or its behavior over time and/or the rapidity with which this coloration develops, is/are ofttimes inadequate.

Moreover, another disadvantage is the fact that DHA has an unfortunate tendency, which is more or less pronounced depending on the nature of the medium in which it is formulated, to become degraded over time, thereby presenting problems of storage-stability and/or of preservation which generally ultimately result in an undesirable yellowing of the compositions comprised thereof.

To overcome these various disadvantages, FR-A-2,698, 267, assigned to the assignee hereof, describes combining DHA with a specific copolymer which serves as a thickener, namely, a crosslinked copolymer of acrylamide/2-acrylamido-2-methylpropanesulfonic acid (including "SEPIGEL 305® "marketed by Seppic).

Although such compositions containing this copolymer are valuable and effectively exhibit improved properties compared with those devoid of same, they do not, however, provide wholly or completely satisfactory results.

SUMMARY OF THE INVENTION

Accordingly, a major object of the present invention is the provision of novel DHA-based cosmetic/artificial tanning compositions which exhibit both an improved self-tanning efficacy and/or activity on the skin (intensity and behavior), as well as an excellent stability.

Briefly, it has now unexpectedly and surprisingly been found that it is possible to improve the skin-coloring or artificial suntanning power associated with the conventional compositions of the prior art based on DHA, by simultaneously introducing into these compositions, on the one hand, at least one compound selected from among the alkylpolysaccharides, in particular alkylpolyglucosides, and, on the other, at least one compound selected from among the fatty alcohols, optionally in admixture with at least one polysaccharide.

All other factors being equal (especially at an identical DHA concentration), it is observed that a self-tanning or artificial suntanning composition in accordance with the invention, by virtue of the presence of an alkylpolysaccharide/fatty alcohol mixture, exhibits systematically, relative to its skin-coloration power and quality (intensity, stability over time and/or to washing), improved properties compared with the same self-tanning composition not containing this specific mixture. Moreover, it has surprisingly also been found that, in the compositions of the invention, the DHA has a substantially increased chemical stability (lesser decomposition over time), and this even at relatively high temperatures.

DETAILED DESCRIPTION OF BEST MODE AND PREFERRED/SPECIFIC EMBODIMENTS OF THE INVENTION

More particularly according to the present invention, novel cosmetic compositions are hereby provided, more especially intended for the artificial tanning of the skin, and which comprise, in a cosmetically acceptable carrier, diluent or vehicle, dihydroxyacetone as the self-tanning agent, and, in addition, at least one alkylpolysaccharide, preferably at least one alkylpolyglucoside, and at least one fatty alcohol.

In one specific embodiment of the present invention, the self-tanning composition may also comprise at least one polysaccharide.

In another specific embodiment of this invention, the combination alkylpolysaccharide/fatty alcohol/ (polysaccharide) which is present in the self-tanning composition is in the form of a mixture comprising (% weight relative to the total weight of the mixture):

(a) from 10% to 80% by weight of alkylpolysaccharide(s), advantageously alkylpolyglucoside(s), (b) from 20% to 90% by weight of fatty alcohol(s) advantageously having from 12 to 22 carbon atoms, and more preferably from 12 to 18 carbon atoms, and (c) optionally, from 0.5% to 5% by weight of a polysaccharide.

In the above mixture, the alkylpolysaccharide preferably has an alkyl moiety which is identical to that of the fatty alcohol, and this mixture then advantageously corresponds to the product directly obtained from the reaction, in acidic medium, between a saccharide and a stoichiometric excess of fatty alcohol, as more fully described below.

Dihydroxyacetone, or DHA, is present in the compositions of the invention in sufficient proportions to confer on or to the skin, after application, a coloration or darkening similar to that obtained following a natural tanning. This DHA is thus generally present in proportions ranging from 0.5% to 10% by weight relative to the total weight of the composition, and preferably from 1% to 6% by weight.

The alkylpolysaccharides suitable for incorporation according to the present invention are compounds which are per se well known to this art, and which are widely used as nonionic surfactants for a broad range of industrial applications. A number of these compounds are, moreover, commercially available.

The use of such alkylpolysaccharides for improving the properties of DHA-based self-tanning cosmetic compositions is, however, conspicuously alien to the prior art.

These compounds and processes for the synthesis thereof are especially described in (1) *Handbook of Surfactants*, by M. R. Porter, Editions Blackie & Son Ltd., pp 142–145 (1991); (2) *Alkylpolyglucosides: An Overview of the Patent Situation*, by H. Fabry et al. (HENKEL), HAPPI review, August 1994, pp 111–115; and (3) WO 92/06,778; these publications (1) to (3) are hereby expressly incorporated by reference.

In general, these compounds may be prepared industrially by reacting, in an acidic medium (sulfuric, hydrochloric or phosphoric acids and the like), a saccharide having an anomeric OH (glucose, dextrose and the like) with a stoichiometric excess of a fatty alcohol, and then optionally distilling off the unetherified fatty alcohol, and, lastly, optionally filtering off the products derived from the possible polycondensation of the saccharides (polysaccharides). The particular reaction conditions to be observed are especially described in WO-92/06,778 indicated above. The compositions which are obtained without effecting removal (distillation) of the excess fatty alcohols, with or without subsequent removal of the residual polysaccharides, thus correspond to the alkylpolysaccharide/fatty alcohol/(polysaccharide) mixtures suitable for the compositions of the present invention. Of course, such mixtures may also be obtained by simply subjecting the various presynthesized constituents to physical mixing.

According to the present invention, the preferred alkylpolysaccharides are those exhibiting at least one, and even more advantageously all, of the following characteristics:

(i) the alkylpolysaccharide comprises a linear or branched alkyl moiety having from 12 to 22 carbon atoms, preferably from 12 to 18 carbon atoms, and even more preferably from 16 to 18 carbon atoms;

(ii) the alkylpolysaccharide comprises at least one saccharide moiety selected from among those of glucose, dextrose, sucrose, fructose, galactose, maltose, maltotriose, lactose, cellobiose, mannose, ribose, dextran, talose, allose, xylose, levoglucosan, cellulose and starch, and preferably this saccharide is selected from among glucose, dextrose, fructose and maltose; more preferably, this saccharide comprises glucose (alkylpolyglucosides);

(iii) the alkylpolysaccharide comprises a polysaccharide backbone containing up to 30 structural units, it being appreciated that each structural unit of the polysaccharide moiety may be in the α- or β-isomeric form, or in the L or D form, and the conformation of the "saccharide" unit in furanoside or pyranoside form with an anomeric oxygen atom.

Mixtures of alkylpolysaccharides can of course also be used, which may differ from each other by the nature of the alkyl moiety and/or the nature of the carrier polysaccharide chain.

The alkylpolysaccharide(s) is/are advantageously present in the self-tanning compositions of the invention in amounts generally ranging from 0.1% to 10% by weight relative to the total weight of the composition, preferably in amounts of from 2% to 8%.

As regards the fatty alcohols which are suitable, whether alone or in admixture, in combination with the alkylpolysaccharides in the self-tanning compositions in accordance with this invention, they may be linear or branched fatty alcohols of synthetic origin or, alternatively, of natural origin, such as, for example, the alcohols obtained from plant materials (copra, cabbage palm, palm and the like), or of animal origin (tallow and the like). Of course, other long-chain alcohols can also be used, such as, for example, ether alcohols or the so-called Guerbet alcohols. Too, certain cuts of longer or shorter alcohols of natural origin, such as, for example, coconut ($C_{12}$ to $C_{16}$) or tallow ($C_{16}$ to $C_{18}$) or diol or cholesterol type compounds may also be used. As indicated above, mixtures of alcohols, such as those obtained especially from tallow or copra, may be used.

In a preferred embodiment of the present invention, the fatty alcohol(s) are selected from among those having from 12 to 22 carbon atoms, and more preferably from 12 to 18 carbon atoms.

Specific fatty alcohols which are suitable according to the present invention include lauryl, cetyl, myristyl, stearyl, palmityl and oleyl alcohols, whether used alone or in admixture.

In addition, and as indicated above, it is particularly advantageous according to this invention to simultaneously employ a fatty alcohol and an alkylpolysaccharide, the alkyl moiety of which is identical to that of the fatty alcohol selected.

The fatty alcohol(s) is/are advantageously present in the self-tanning compositions of the invention in amounts generally ranging from 0.1% to 10% by weight relative to the total weight of the composition, preferably in amounts of from 0.4% to 9% by weight.

Commercially available products suitable for the present invention include those marketed under the trademark EMULGADE® PL 1618 by HENKEL, or those marketed under the trademark MONTANOV 68® by SEPPIC. The product designated MONTANOV 68® is particularly suitable.

The self-tanning compositions in accordance with the invention may be provided in the form of creams, milks, gels, cream gels, oil-in-water emulsions, vesicular dispersions, fluid lotions, in particular vaporizable fluid lotions, or any other form generally employed in cosmetics, in particular that usually suitable for self-tanning cosmetic compositions.

The cosmetically acceptable medium (or vehicle, diluent or carrier) for these compositions conventionally comprises water, a mixture of water and one or more organic solvents, or a solvent or a mixture of cosmetically acceptable organic solvents. This medium also contains, in a preferred embodiment, cosmetically acceptable fatty substances and/or silicones.

The solvents are advantageously selected from among the polyhydric alcohols such as, for example, glycerol, ethylene glycol, propylene glycol, diethylene glycol and sorbitol, or from water-soluble lower alcohols such as ethanol, isopropanol or butanol.

The various fatty substances which are suitable, whether used alone or in admixture, are advantageously selected from among oils of plant, animal or inorganic origin, natural or synthetic waxes, and the like.

Exemplary oils which may comprise the fatty phase include:

(1) mineral oils such as paraffin oil and liquid paraffin;

(2) oils of animal origin such as perhydrosqualene;

(3) oils of plant origin such as sweet almond oil, avocado oil, castor oil, olive oil, jojoba oil, sesame oil, groundnut oil, grapeseed oil, rapeseed oil, copra oil, hazelnut oil, shea butter, palm oil, apricot stone oil, calophyllum oil, rice bran oil, maize germ oil, wheatgerm oil, soybean oil, sunflower oil, evening primrose oil, safflower oil, passion flower oil and rye oil;

(4) synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and lanolic acid-derived esters such as isopropyl lanolate and isocetyl lanolate, isoparaffins and poly-α-olefins.

Other oils suitable for formulation into the compositions of the invention include the $C_{12}$–$C_{15}$ fatty alcohol benzoates (Finsolv TN marketed by FINETEX), acetylglycerides, alcohol and polyalcohol octanoates and decanoates such as those of glycol and glycerol, alcohol and polyalcohol ricinoleates such as those of cetyl, fatty acid triglycerides such as caprylic/capric triglycerides, $C_{10}$–$C_{18}$ saturated fatty acid triglycerides, fluorinated and perfluorinated oils, lanolin, hydrogenated lanolin, acetylated lanolin, silicone oils, whether volatile or nonvolatile, or organic solutions of organosiloxane gums and/or resins.

It will of course be appreciated that the compositions according to the invention may also contain one or more conventional lipophilic or hydrophilic cosmetic adjuvants or additives, in particular those which are typically formulated into cosmetic artificial suntan compositions.

Exemplary conventional cosmetic adjuvants and additives suitable for formulation into the aqueous phase and/or into the fatty phase of the compositions of the invention (depending on their water- and/or fat-soluble character), are, in particular, ionic or nonionic thickeners, demulcents, softeners, antioxidants, opacifiers, stabilizers, emollients, insect repellents, organic sunscreens which are active in the UV-A and/or UV-B range, photoprotective mineral pigments and nanopigments, moisturizing agents, vitamins, perfumes, fragrances, preservatives, fillers, sequestrants, colorants, or any other constituent typically formulated into artificial suntan preparations.

The present invention also features the use of the compositions described above, as, or for the formulation of, cosmetic compositions for the artificial tanning or darkening of the skin. The compositions may then be formulated as creams, milks, ointments, cream gels, or, alternatively, as fluid lotions, in particular as vaporizable fluid lotions, or any other appropriate form.

The artificial tanning or darkening of the human epidermis according to this invention entails applying to the skin an effective amount of a cosmetic composition as described above, for a period of time sufficient to elicit the desired response.

In order to further illustrate the present invention and the advantages thereof, the following specific examples are given, it being understood that same are intended only as illustrative and in nowise limitative.

EXAMPLE 1

In this example, specific artificial tanning compositions based on dihydroxyacetone (5% by weight) were prepared and compared, one composition being in accordance with the invention (C1) and containing an alkylpolysaccharide/fatty alcohol mixture ("MONTANOV 68" marketed by Seppic), the other being comparative (C2), differing from C1 only in that it contained, instead of said mixture, a crosslinked acrylamide/2-acrylamido2-methylpropanesulphonic acid copolymer as described in FR-A-2,698,267 ("SEPIGEL 305" marketed by Seppic), this comparative composition being considered the best performing prior art composition.

The chemical compositions (% by weight relative to the total weight of the formulation) of these two formulations were as follows:

Phase A
(a) Silicone oil 10%
(b) $C_{12}$–$C_{15}$ alcohol benzoate ("FINSOLV TN" marketed by WITCO) 5%
(c) 4-(tert-butyl)-4'-methoxydibenzoylmethane (sunscreen "PARSOL 1789" marketed by GIVAUDAN) 0.5%
(d) 4-methylbenzylidenecamphor (sunscreen "EUSOLEX 6300" marketed by MERCK) 1.5%
(e) MONTANOV 68 [1/](for composition C1) 7.5% or
(e') SEPIGEL 305 (for composition C2) 3%

[1/] MONTANOV 68 is a commercially available product whose composition corresponds to that of the reaction product described in Example 1 of Seppic's WO 92/06,778.

Phase B
(a) Dihydroxyacetone 5%
(b) Water 30%

Phase C
(a) Glycerol 3%
(b) Sorbitol in aqueous solution at 70% 2%
(c) Water qs 100%

Phase D
(a) Perfume qs
(b) Preservatives qs

The procedure which was carried out for preparing these compositions was as follows: the fatty phase (A) and aqueous phase (C) were both previously heated to a temperature on the order of 90° C. The aqueous phase (C) was then added to the fatty phase (A), with vigorous stirring of the latter using a MORITZ turbine (1,000 rpm). Lastly, the phase (B) was first added and then the phase (D) into the resulting emulsion, at about 40° C.

The skin-coloration strength of the two compositions C1 and C2 thus obtained was then compared. The skin-coloration strength was assessed by means of the following test: the compositions were applied at the rate of 2 mg/cm² of skin (squares of about 6 cm²), to the forearms of three control individuals (P1, P2 and P3) and the colorimetric variation of the value L (chromatic coordinate of luminance, measured using a MINOLTA CM 1000 colorimeter) was measured on these forearms before (To) and after (5 hours and 24 hours) application, such as to determine a mean absolute value ΔL which provides the intensity of the coloration obtained on the skin after application (the higher the mean ΔL, the more intense the coloration):

$$\Delta L(5H) = L_{T_0} - L_{T_{5h}}$$

$$\Delta L(24H) = L_{T_0} - L_{T_{24h}}$$

In order to also quantify the water-stability of the colors obtained, the treated forearms of each test subject were washed with soap, this washing being after the measurement at $T_{5h}$ and before the measurement at $T_{24h}$.

The results obtained are reported in the Table below. These results clearly show that the composition C1 in accordance with the invention provides on the skin a coloration which was significantly more intense than the comparative composition C2, both 5 hours and 24 hours after application, and this even after an intermediate washing.

Moreover, for the above two compositions, the stability of DHA after a 2-month storage at room temperature, on the one hand, and at 45° C., on the other, was quantified by HPLC analysis using a MERCK LICHROSPHER SI 100 column (eluent:mixture ethanol (5%)/$Cl_2CH_2$ (95%) by volume; pressure 750 psi) thereby permitting monitoring over time the level of undegraded DHA.

The results obtained are also reported in the Table below.

These results show clearly that DHA is preserved better at 45° C. in the composition in accordance with the invention than in the comparative composition.

TABLE

| COMPOSITION | COLOR ($\Delta L$)[1] | | LEVEL OF PRESERVATION OF DHA (%) | |
|---|---|---|---|---|
| | after 5 h | after 24 h | after 2 months at room temperature | after 2 months at 45° C. |
| C1 (invention) | 3.2 | 3.45 | 100 | 89 |
| C2 (comparative) | 2.9 | 2.6 | 100 | 73 |

[1] :mean

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic composition adopted for the artificial tanning and/or darkening of human skin, comprising an effective artificial tanning amount of dihydroxyacetone, in immixture with at least one alkylpolysaccharide and at least one fatty alcohol, and, optionally, at least one polysaccharide.

2. The cosmetic artificial tanning and/or darkening composition as defined by claim 1, comprising a cosmetically acceptable vehicle, diluent or carrier therefor.

3. The cosmetic artificial tanning and/or darkening composition as defined by claim 2, said at least one alkylpolysaccharide comprising from 10% to 80% by weight of the total weight of said alkylpolysaccharide/fatty alcohol/optional polysaccharide immixture.

4. The cosmetic artificial tanning and/or darkening composition as defined by claim 3, said at least one fatty alcohol comprising from 20% to 90% by weight of the total weight of said alkylpolysaccharide/fatty alcohol/optional polysaccharide immixture.

5. The cosmetic artificial tanning and/or darkening composition as defined by claim 4, comprising from 0.5% to 5% by weight of said at least one polysaccharide relative to the total weight of the alkylpolysaccharide/fatty alcohol/polysaccharide immixture.

6. The cosmetic artificial tanning and/or darkening composition as defined by claim 2, comprising from 0.1% to 10% by weight of said at least one alkylpolysaccharide.

7. The cosmetic artificial tanning and/or darkening composition as defined by claim 6, comprising from 2% to 8% by weight of said at least one alkylpolysaccharide.

8. The cosmetic artificial tanning and/or darkening composition as defined by claim 2, comprising from 0.1% to 10% by weight of said at least one fatty alcohol.

9. The cosmetic artificial tanning and/or darkening composition as defined by claim 8, comprising from 0.4% to 9% by weight of said at least one fatty alcohol.

10. The cosmetic artificial tanning and/or darkening composition as defined by claim 2, comprising from 0.5% to 10% by weight of dihydroxyacetone.

11. The cosmetic artificial tanning and/or darkening composition as defined by claim 10, comprising from 1% to 6% by weight of dihydroxyacetone.

12. The cosmetic artificial tanning and/or darkening composition as defined by claim 2, the alkyl moiety of said at least one alkylpolysaccharide having from 12 to 22 carbon atoms.

13. The cosmetic artificial tanning and/or darkening composition as defined by claim 12, said alkyl moiety having from 12 to 18 carbon atoms.

14. The cosmetic artificial tanning and/or darkening composition as defined by claim 13, said alkyl moiety having from 16 to 18 carbon atoms.

15. The cosmetic artificial tanning and/or darkening composition as defined by claim 2, the saccharide moiety of said at least one alkylpolysaccharide comprising glucose, dextrose, sucrose, fructose, galactose, maltose, maltotriose, lactose, cellobiose, mannose, ribose, dextran, talose, allose, xylose, levoglucosan, cellulose or starch.

16. The cosmetic artificial tanning and/or darkening composition as defined by claim 15, the saccharide moiety of said at least one alkylpolysaccharide comprising glucose, dextrose, fructose or maltose.

17. The cosmetic artificial tanning and/or darkening composition as defined by claim 16, the saccharide moiety of said at least one polysaccharide comprising glucose.

18. The cosmetic artificial tanning and/or darkening composition as defined by claim 2, said at least one fatty alcohol having from 12 to 22 carbon atoms.

19. The cosmetic artificial tanning and/or darkening composition as defined by claim 18, said at least one fatty alcohol having from 12 to 18 carbon atoms.

20. The cosmetic artificial tanning and/or darkening composition as defined by claim 2, the alkyl moiety of said at least one alkylpolysaccharide having the same number of carbon atoms as the alkyl moiety of said at least one fatty alcohol.

21. The cosmetic artificial tanning and/or darkening composition as defined by claim 2, further comprising at least one cosmetically acceptable adjuvant or additive.

22. The cosmetic artificial tanning and/or darkening composition as defined by claim 21, said at least one adjuvant or additive comprising an ionic or nonionic thickener, demulcent, softener, antioxidant, opacifier, stabilizer, organic sunscreen, emollient, insect repellent, filler, moisturizer, vitamin, perfume, preservative, sequestering agent, colorant, photoprotective inorganic nanopigment or pigment, or mixture thereof.

23. A method for artificially tanning and/or darkening human skin, comprising topically applying thereto an effective amount of the cosmetic artificial tanning and/or darkening composition as defined by claim 1.

24. The cosmetic artificial tanning and/or darkening composition as defined by claim 1, comprising a cream, gel, ointment, cream gel, milk or lotion.

* * * * *